(12) United States Patent
Schlomka et al.

(10) Patent No.: US 7,418,073 B2
(45) Date of Patent: Aug. 26, 2008

(54) COMPUTED TOMOGRAPHY DEVICE AND METHOD WITH THREE-DIMENSIONAL BACKPROJECTION

(75) Inventors: Jens-Peter Schlomka, Hamburg (DE); Michael Graβ, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 124 days.

(21) Appl. No.: 10/534,159

(22) PCT Filed: Oct. 24, 2003

(86) PCT No.: PCT/IB03/04749

§ 371 (c)(1), (2), (4) Date: May 5, 2005

(87) PCT Pub. No.: WO2004/044848

PCT Pub. Date: May 27, 2004

(65) Prior Publication Data

US 2006/0153328 A1    Jul. 13, 2006

(30) Foreign Application Priority Data

Nov. 11, 2002 (DE) ................. 102 52 662

(51) Int. Cl.
*G01N 23/201* (2006.01)

(52) U.S. Cl. ................. 378/6; 378/70; 378/86; 378/87; 378/88

(58) Field of Classification Search ............... 378/4, 378/21, 901, 16, 19, 57, 70, 71, 86, 87, 88, 378/90, 6; 382/128, 134; 600/437; 708/813
See application file for complete search history.

(56) References Cited

U.S. PATENT DOCUMENTS

| 5,170,439 | A |   | 12/1992 | Zeng et al. |
|---|---|---|---|---|
| 5,270,926 | A |   | 12/1993 | Tam |
| 5,625,660 | A | * | 4/1997 | Tuy ............................. 378/15 |
| 5,881,123 | A |   | 3/1999 | Tam |
| 5,907,593 | A |   | 5/1999 | Hsieh et al. |
| 6,002,739 | A |   | 12/1999 | Heumann |
| 6,125,163 | A |   | 9/2000 | Barth et al. |

(Continued)

FOREIGN PATENT DOCUMENTS

WO    WO 03/085390 A2    10/2003

OTHER PUBLICATIONS

Stefan M. Schneider, Jens-Peter Schlomka, and Geoffrey Harding, "Coherent Scatter Computed Tomography Applying a Fan-Beam Geometry," Medical Imaging 2001: Physics of Medical Imaging, Proceedings of SPIE vol. 4320 (2001), p. 754-763.*

(Continued)

*Primary Examiner*—Allen C. Ho (57) ABSTRACT

The invention relates to a computed tomography method in which an examination zone is irradiated along a circular trajectory by a fan-shaped radiation beam. Radiation coherently scattered in the examination zone is measured by a detector unit, the variation in space of the scatter intensity in the examination zone being reconstructed from said measuring values. Reconstruction is performed by back projection in a volume which is defined by two linearly independent vectors of the rotational plane and a wave vector transfer.

16 Claims, 6 Drawing Sheets

U.S. PATENT DOCUMENTS

| | | | |
|---|---|---|---|
| 6,285,733 | B1 | 9/2001 | Proksa et al. |
| 6,426,989 | B2 * | 7/2002 | Grass et al. .................... 378/4 |
| 6,470,067 | B1 * | 10/2002 | Harding ........................ 378/19 |
| 6,744,845 | B2 * | 6/2004 | Harding et al. ............... 378/16 |
| 2001/0038678 | A1 * | 11/2001 | Grass et al. .................... 378/4 |
| 2002/0150202 | A1 * | 10/2002 | Harding et al. ............... 378/16 |
| 2003/0133533 | A1 | 7/2003 | Bruder et al. |

OTHER PUBLICATIONS

U. van Stevendaal, J.-P. Schlomka, A. Thran, J. Delfs, and H. Barschdorf, "A new reconstruction algorithm for energy-resolved coherent scatter computed tomography," Medical Imaging 2005: Image Processing, Proceedings of SPIE vol. 5747 (2005), p. 2083-2093.*

Grass, M., et al.; 3D cone-beam CT reconstruction for circular trajectories; Phys. Med. Biol.; 2000; 45:329-347.

* cited by examiner

COMPUTED TOMOGRAPHY DEVICE AND METHOD WITH THREE-DIMENSIONAL BACKPROJECTION

The invention relates to a computed tomography method in which an examination zone is irradiated along a circular trajectory by a fan-shaped radiation beam and in which a detector unit detects primary radiation and radiation which is coherently scattered in the examination zone. The invention also relates to a computer tomograph for carrying out such a method as well as to a computer program for controlling the computer tomograph.

In known methods of the kind set forth radiation which is coherently scattered in the examination zone is measured by a detector unit; the variation in space of the scatter intensity in the examination zone is then reconstructed from said measuring values. The reconstruction is usually carried out by means of iterative methods based on algebraic reconstruction techniques (ART) in which a reconstruction of the entire irradiated examination zone is necessary. A reconstruction of a part of the examination zone is not possible. Moreover, the iterative methods require a large amount of calculation work and hence lead to comparatively long reconstruction times. Alternative methods involve two-dimensional reconstruction techniques based on back projection; in these techniques such large distances exist or are assumed between the examination zone and the detector unit that an unambiguous relationship exists between the point of incidence of a scattered ray on the detector unit and the scatter angle. However, this geometry cannot be realized in medical applications, so that the two-dimensional back projection produces inaccurate results only.

Therefore, it is an object of the present invention to provide a method, a computer tomograph as well as a computer program which enable a faster reconstruction of the scatter intensity distribution in the examination zone while taking into account the actual geometry in medical applications.

In respect of the method this object is achieved in accordance with the invention by means of a computed tomography method which comprises the steps of generating, using a radiation source and a diaphragm arrangement which is arranged between the examination zone and the radiation source, a fan beam which traverses an examination zone or an object present therein, generating relative motions, comprising a rotation about an axis of rotation, between the radiation source on the one side and the examination zone or the object on the other side, acquiring measuring values which are dependent on the intensity of the radiation by means of a detector unit which detects, during the relative motions, the primary radiation from the fan beam and radiation which is coherently scattered in the examination zone or on the object, reconstructing a CT image of the examination zone from the measuring values, during which reconstruction a back projection is carried out in a volume which is defined by two linearly independent vectors of the rotational plane and a wave vector transfer.

The scatter intensity is dependent not only on the material but also on the scatter angle and the wavelength of the radiation. A back projection in a volume defined by two linearly independent vectors of the rotational plane and a wave vector transfer, however, has the advantage that the scatter intensity thus parameterized is dependent exclusively on the scatter material, because the wave vector transfer is known to be proportional to the product of the inverse wavelength and the sine of half the scatter angle. In this context the scatter angle is the angle which is enclosed by the path of the scattered ray relative to the path that the ray would have followed in the absence of the scattering process.

The scattered rays have a curved shape in said volume. Taking the curved shape of the scattered rays into account for the back projection enhances the quality of the reconstructed scatter intensity distribution.

According to a preferred reconstruction method the measuring values are weighted prior to the back projection. Such weighting takes into account the fact that the effectiveness of the detector surface decreases as the scatter angle increases and also that the radiation density decreases as the distance between the point of incidence of the scattered ray on the detector unit and the scatter center increases. The effective detector surface is the detector surface projected in a plane perpendicular to the path of the detected ray. In another embodiment, weighting takes into account the fact that the radiation density decreases as the distance between the radiation source and the scatter center increases. The quality of the reconstructed scatter intensity distribution is enhanced when such effects are taken into account.

Another embodiment describes a preferred reconstruction method which requires less calculation work in comparison with other methods and offers a favorable image quality nevertheless.

A computer tomograph for carrying out the method in accordance with the invention is also disclosed.

Another embodiment defines a computer program for controlling a computer tomograph The invention will be described in detail hereinafter on the basis of an embodiment and with reference to a drawing; therein:

Figure 1:
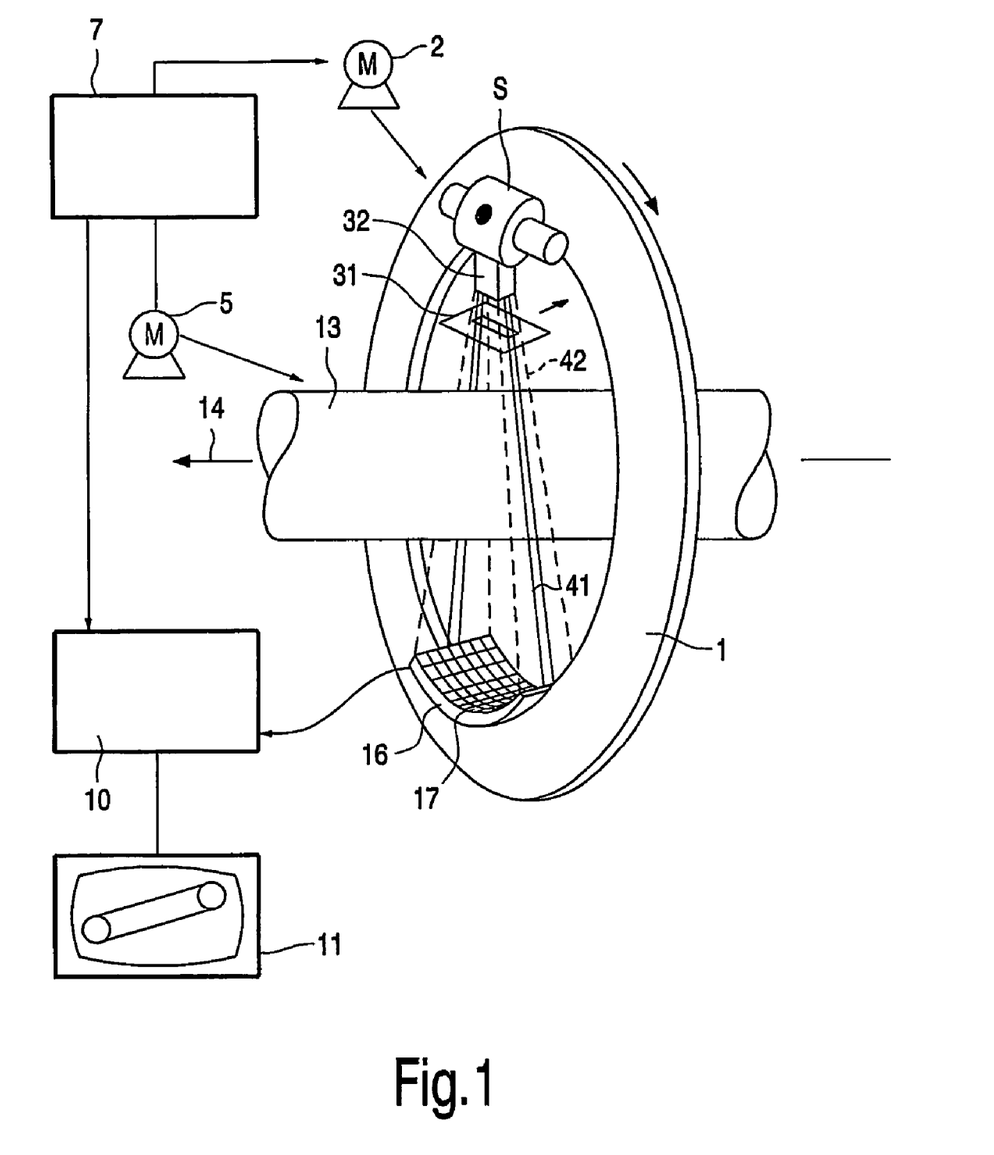
FIG. 1 shows a computer tomograph which is suitable for carrying out the method in accordance with the invention.

The computer tomograph shown in FIG. 1 comprises a gantry 1 which is capable of rotation about an axis of rotation 14. To this end, the gantry 1 is driven by a motor 2 at a preferably constant, but adjustable angular speed. A radiation source S, for example, an X-ray source, is mounted on the gantry 1. A diaphragm arrangement 31 defines a radiation fan beam 41 which is used for the examination and is denoted by solid lines in FIG. 1. The fan beam 41 extends perpendicularly to the axis of rotation 14 and has small dimensions in the direction thereof, for example, 1 mm. Between the diaphragm arrangement 31 and the radiation source S there may be arranged a second diaphragm device 32 which forms a conical radiation beam 42 from the radiation generated by the X-ray source S. The conical radiation beam 42, which would arise in the absence of the diaphragm arrangement 31, is denoted by dashed lines.

The fan beam 41 traverses a cylindrical examination zone 13 in which an object, for example, a patient on a patient table (both not shown) or also a technical object may be situated. After having traversed the examination zone 13, the fan beam 41 is incident on a detector unit 16 which is attached to the gantry 1 and comprises a measuring surface 17 with a plurality of detector elements arranged in the form of a matrix. The detector elements are arranged in rows and columns. The detector columns extend parallel to the axis of rotation 14. The detector rows are situated in planes which extend perpendicularly to the axis of rotation, that is, preferably on an arc of a circle around the radiation source S. However, they may also have a different shape, for example, the shape of an arc of a circle around the axis of rotation, or be rectilinear. Generally speaking, the detector rows comprise substantially more detector elements (for example, 1000) than the detector columns (for example, 16).

The fan beam 41, the examination zone 13 and the detector unit 16 are adapted to one another. In a plane perpendicular to the axis of rotation 14 the dimensions of the fan beam 41 are chosen to be such that the examination zone 13 is fully irradiated and the length of the rows of the detector unit 16 is such that the fan beam 41 can be detected completely. The fan beam is incident on the central detector row (rows).

When a technical object is concerned instead of a patient, the object can be rotated during an examination while the radiation source S and the detector unit 16 remain stationary. The examination zone 13, or the object or the patient table, can be displaced parallel to the axis of rotation 14 by means of a motor 5. As an equivalent, however, the gantry could also be displaced in this direction.

When the motors 2 and 5 operate simultaneously, the radiation source S and the detector unit 16 describe a helical trajectory relative to the examination zone 13. However, when the motor 5 for the displacement in the direction of the axis of rotation 14 is stationary and the motor 2 rotates the gantry, a circular trajectory is obtained for the radiation source S and the detector 16 relative to the examination zone 13. Hereinafter only the circular trajectory will be considered.

Figure 2:
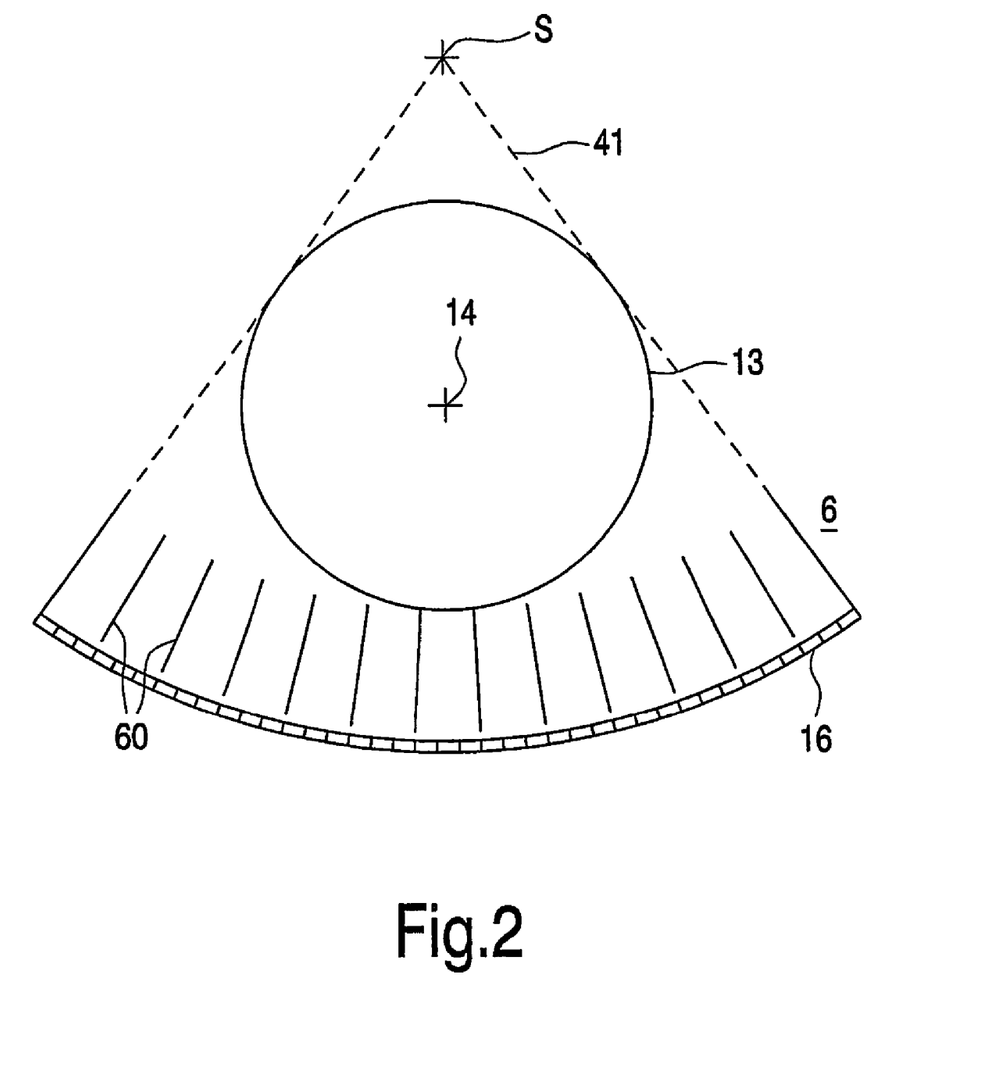
FIG. 2 is a diagrammatic cross-sectional view of the computer tomograph of FIG. 1 in the direction of the axis of rotation.

FIG. 2 shows that between the examination zone 13 and the detector unit 16 there is arranged a collimator arrangement 6 which comprises a plurality of blades 60. The blades 60 consist of a material which strongly absorbs the X-rays and are situated in planes which extend parallel to the axis of rotation 14 and intersect one another at the focus of the radiation source S. Their spacing may amount to, for example, 1 cm and each blade 60 may have a dimension of, for example, 20 cm in the plane of drawing. The collimator arrangement 6 thus subdivides the fan beam 41 into a number of neighboring segments, so that essentially a column of detector elements is struck by primary or scattered radiation from one segment only.

The measuring values acquired by the detector unit 16 are applied to an image processing computer 10 which is connected to the detector unit 16, for example, via a wireless data transmission. The image processing computer 10 reconstructs the scatter intensity distribution in the examination zone 13 and reproduces it, for example, on a monitor 11. The two motors 2 and 5, the image processing computer 10, the radiation source S and the transfer of the measuring values from the detector unit 16 to the image processing computer 10 are controlled by a control unit 7.

In other embodiments the acquired measuring values can first be applied to one or more reconstruction computers for reconstruction, which reconstruction computers apply the reconstructed data to the image processing computer, for example, via an optical fiber cable.

Figure 3:
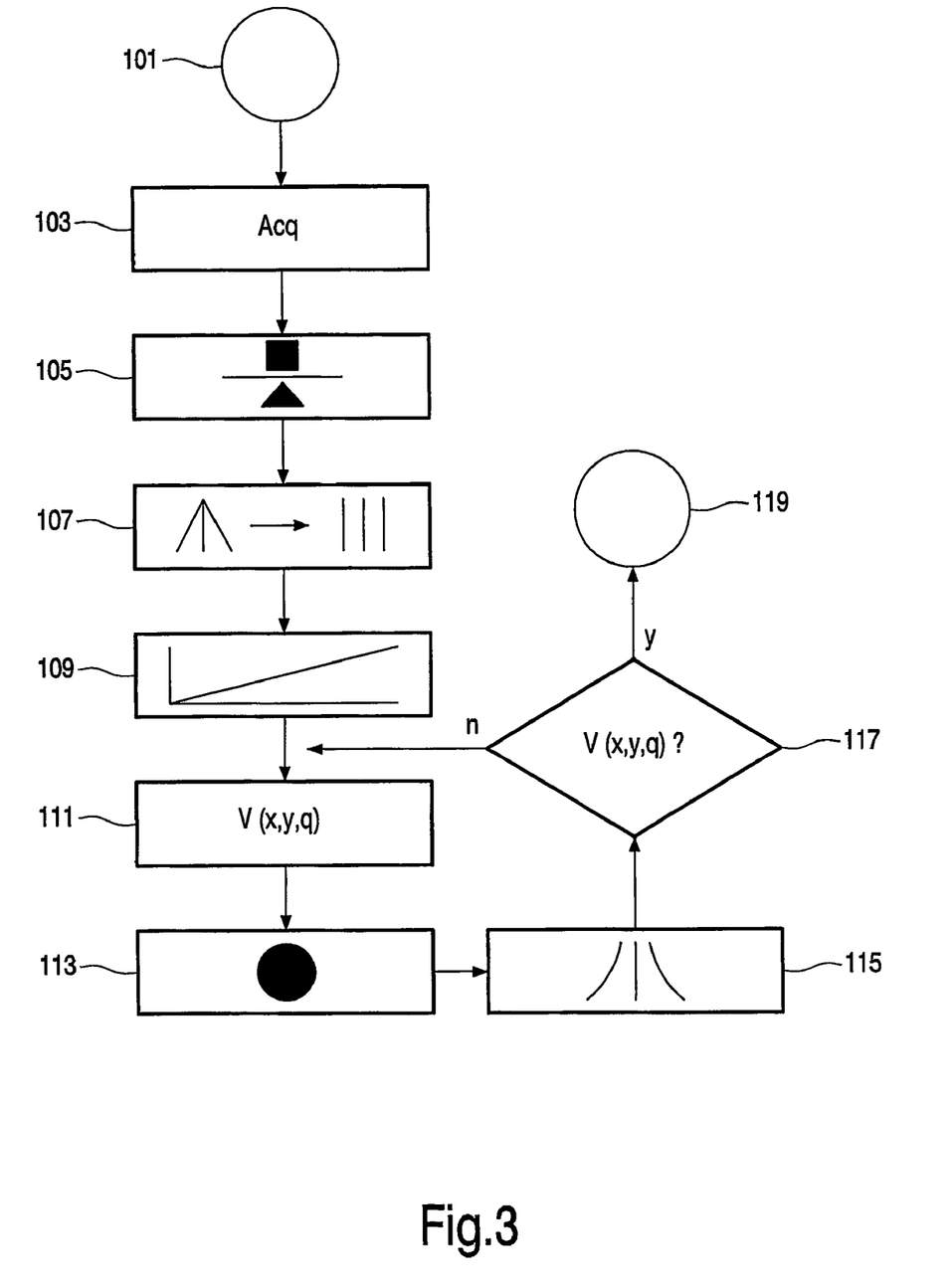
FIG. 3 shows a flow chart of a version of the method in accordance with the invention.

FIG. 3 shows a flow chart illustrating the execution of a version of a measuring and reconstruction method that can be carried out by means of the computer tomograph shown in FIG. 1.

After the initialization in the step 101, the gantry rotates at a constant angular speed. In the step 103 the radiation of the radiation source S is switched on so that the detector unit 16 can detect the primary and the scattered radiation from a plurality of angular positions. The detector element or elements at the center of each detector column detect essentially the primary radiation, whereas the scattered radiation (secondary radiation) is detected by the detector elements which are situated further nearer to the ends of a column.

Figure 4:
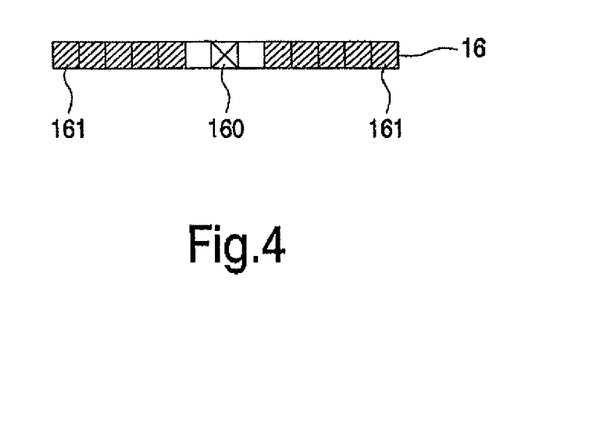
FIG. 4 is a plan view of a column of detector elements.

The foregoing is diagrammatically indicated in FIG. 4 which is a plan view of a column of detector elements. The detector elements 161 which detect the scattered radiation are denoted by simple shading whereas the detector element 160 which is situated at the center and detects the primary radiation is marked by a cross. In other radiation sources, notably in radiation sources having a larger focus, the primary radiation could also be detected by more than one detector element. To both sides of the central detector element there are situated detector elements which are struck by scattered radiation, but also by a (reduced) amount of primary radiation (white elements neighboring 160) because of the finite dimensions of the focus of the radiation source. In this embodiment scattered radiation is considered to be only the radiation which is measured by the detector elements denoted by shading in the drawing.

The scatter intensity is dependent inter alia on the energy of the scattered X-ray quantum. Therefore, the energy of the scattered X-ray quantum must either be measured, implying that the detector elements should be capable of measuring in an energy-resolved fashion, or use must be made of X-rays with quantum energies from an as small as possible range (monochromatic X-rays in the ideal case). There are various possibilities for minimizing the energy difference of the X-ray quanta relative to their energy:

The use of suitable filter materials, for example, copper in the primary beam. As a result, the soft X-rays generated by an X-ray source, that is, X-rays having a low quantum energy, are suppressed to a high degree.

Additionally, the voltage of an X-ray tube can be optimized with respect to the selected filter.

Finally, the so-called "balanced filter" technique can be applied. According to this technique the data is acquired twice and each time filters which have a slightly different atomic number and whose K edge is used for filtering are then situated in the beam path. Subsequently, the difference signal from the two measurements is extracted.

In the step 105 the measuring values of the scattered radiation are normalized. The measuring values of each radiation source position of the scattered radiation are then divided by the measuring values of those primary rays which have caused the scattered rays.

In the step 107 the measuring values are subjected to a rebinning operation. Each measuring value is then associated with a line from the detector element in which the measuring value has been detected to the radiation source position. Thus, it is assumed that rays of the fictitious, conical radiation beam 42 have caused the measuring values without the rays having been scattered. Due to the rebinning operation the measuring values are resorted as if they had been measured by means of a different radiation source (a circular radiation source capable of emitting mutually parallel fan beams) and a different detector (a flat, rectangular virtual detector).

Figure 5:
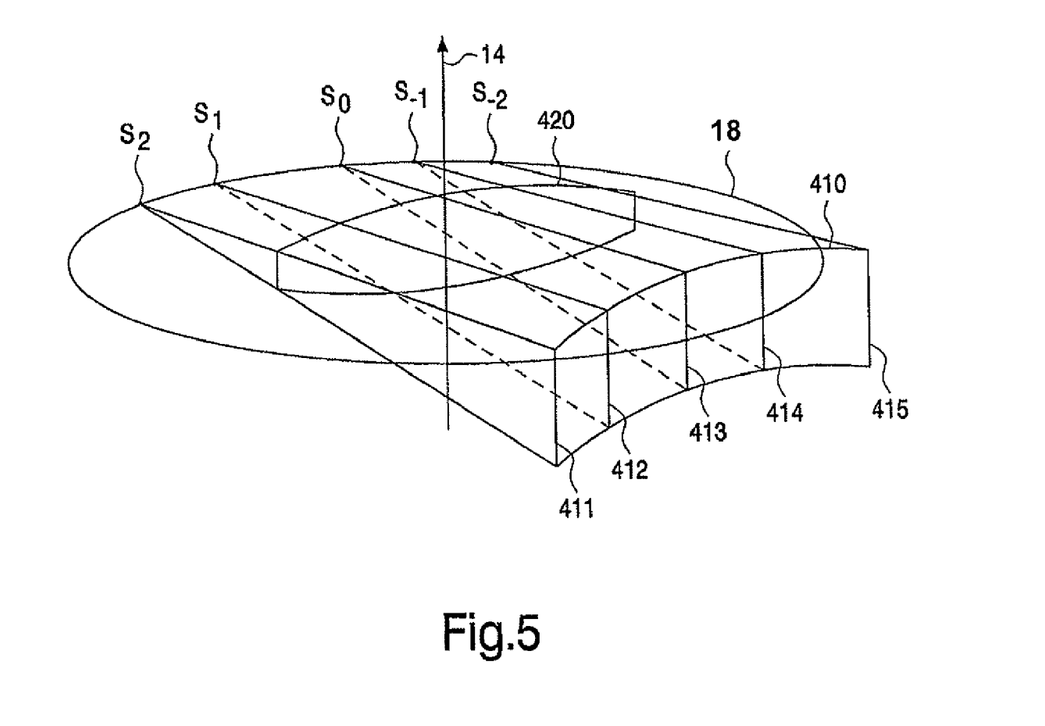
FIG. 5 is a diagrammatic representation of the arrangement of virtual radiation source.

This will be described in detail with reference to FIG. 5. Therein, the reference numeral 18 denotes the circular trajectory along which the radiation source irradiates the examination zone. The reference numeral 413 denotes a fan-shaped radiation beam which emanates from the radiation source position $S_0$ and whose rays propagate in a plane containing the axis of rotation 14. The conical radiation beam emitted by the radiation source in the position $S_0$ may be assumed to consist of a plurality of flat fan beams which are situated in planes which are parallel to the axis of rotation 14 which intersect in the radiation source position. FIG. 5 shows only a single one of these fan beams, that is, the fan beam 413.

Moreover, FIG. 5 also shows further fan beams 411, 412 and 414, 415 which extend parallel to the fan beam 413 and are situated in planes which are parallel to one another and to the axis of rotation 14. The associated radiation source positions $S_{-2}$, $S_{-1}$ and $S_1$, $S_2$ are occupied by the radiation source S before and after reaching the radiation source position $S_0$, respectively. All rays in the fan beams 411 to 415 have the same projection angle. The projection angle is the angle enclosed by the planes of the fan beams with respect to a reference plane which is parallel to the axis of rotation 14.

Figure 6:
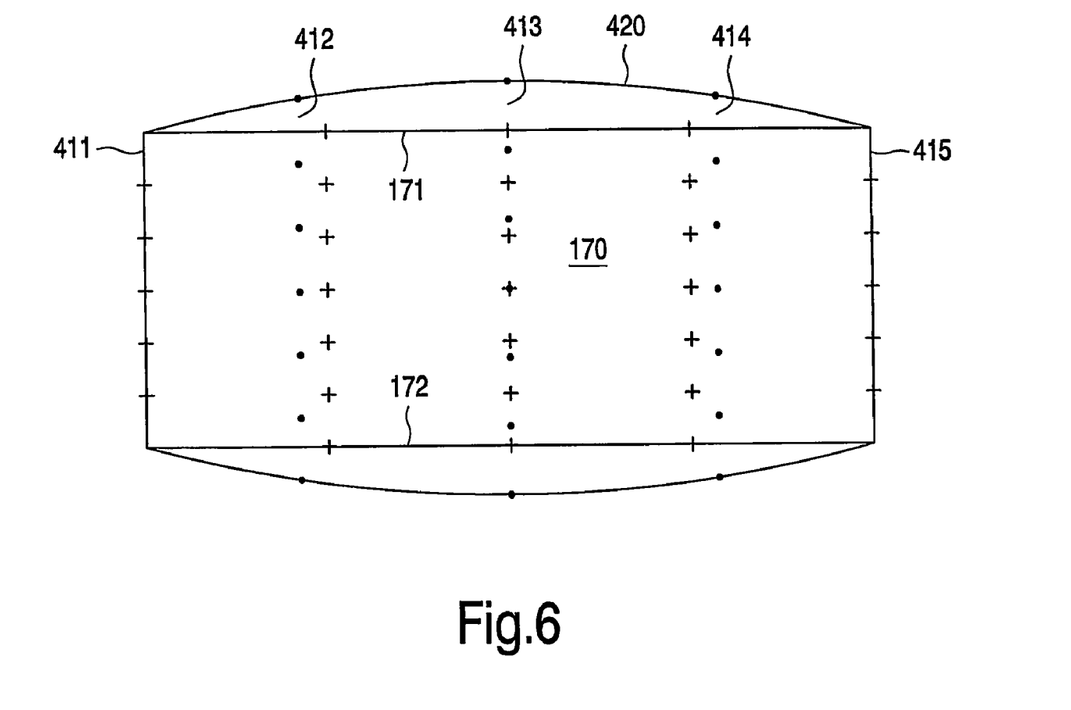
FIG. 6 shows a cross-section through the rays of the virtual radiation sources.

The fan beams 411 to 415 define a radiation beam 410 having a tent-like shape. FIGS. 5 and 6 show the sectional area 420 which is obtained when the radiation beam 410 is intersected by a plane which contains the axis of rotation 14 and extends perpendicularly to the planes of the fan beams 411 to 415. The two edges of the sectional area 420 which intersect the axis of rotation are curved. This curvature is due to the fact that the radiation source position at the center (for example, $S_0$) are situated further from the sectional plane than those at the edge (for example, $S_2$ or $S_{-2}$) and that the fan beams all have the same angle of aperture. For each group of fan beams, therefore, a rectangular virtual detector 170 is defined in the plane sectional area 420, the edges 171 and 172 of said virtual detector being given by the dimensions of the outer fan beams 411 and 415 in the plane sectional area.

FIG. 6 also shows (marked by round dots) the puncture points of some rays, contained in the fan beams 411 . . . 415, through said virtual detector. Finally, crosses mark the supporting points of a regular Cartesian grid. The puncture points and the supporting points usually do not coincide. From the measuring values for the puncture points, therefore, the measuring values at the equidistant supporting points within the virtual detector 170 have to be determined. Such rebinning is described in detail in DE 198 45 133 A1 whereto reference is explicitly made herein.

In the step 109 the measuring values of the scattered rays as produced by the rebinning are subjected to one-dimensional filtering with a factor which increases ramp-like as a function of the spatial frequency. To this end, each time successive values are taken into account in a direction parallel to the plane of rotation, that is, along a row of the virtual detector. This filtering is carried out along each row of the virtual detector for all projection angles.

In other embodiments the rebinning could also be omitted. It is known that in that case the filtering must be modified because the detector unit is curved, for example in the form of an arc around the radiation source or around the axis of rotation.

The filtered measuring values are subsequently used for the reconstruction of the scatter intensity distribution in the examination zone by back projection.

The back projection is carried out in a volume which is defined by the vectors $\vec{x}$, $\vec{y}$ and $\vec{q}$, the unity vectors $\vec{x}$ and $\vec{y}$ being situated in the rotational plane and being oriented horizontally and vertically, respectively, whereas the wave vector transfer $\vec{q}$ is oriented parallel to the axis of rotation. In other embodiments two other, linearly independent vectors of the plane of rotation can be used instead of the vectors $\vec{x}$ and $\vec{y}$. As has already been stated, the amount of the wave vector transfer $\vec{q}$ is proportional to the product of the inverse wavelength λ of the scattered X-ray quanta and the sine of one half of the scatter angle Θ:

$$q=(1/\lambda)\sin(\Theta/2) \tag{1}$$

Figure 7:
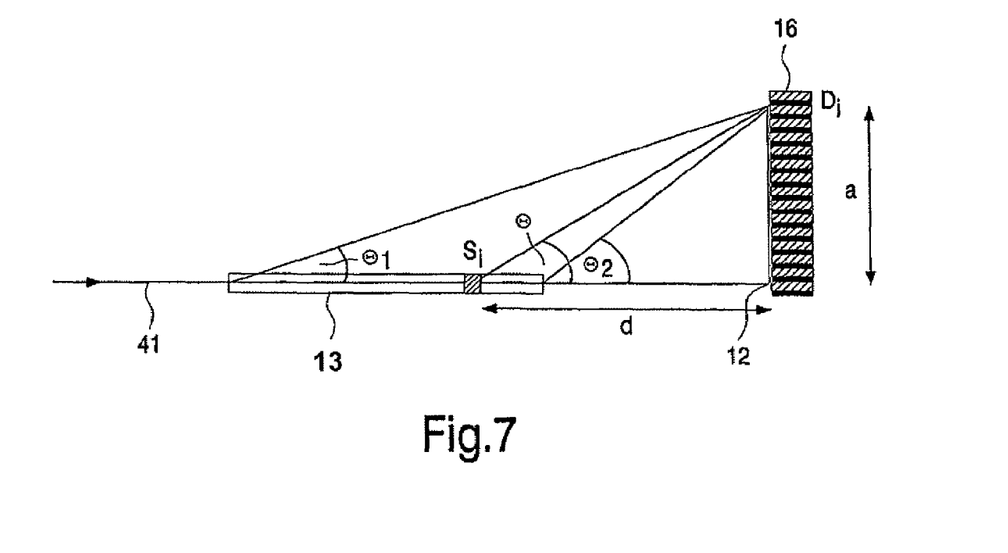
FIG. 7 is a diagrammatic sectional view of the irradiated examination zone and the detector in the direction of the plane of rotation.

The scatter angle Θ can be determined on the basis of the arrangement of the examination zone 13 irradiated by the fan beam 41 and the detector unit 16 as shown in FIG. 7. As opposed to known two-dimensional methods based on back projection, this Figure takes into account the real geometry in medical applications. For one or each detector element $D_i$ this gives rise to different scatter angles Θ which are calculated in conformity with the following equation:

$$\Theta=\arctan(a/d) \tag{2}$$

Therein, d denotes the distance of a scatter center $S_i$ and a denotes the distance between the detector element $D_i$ and the foot 12 of the detector.

The detector $D_i$ detects rays which have been scattered at the angles $\Theta_1<\Theta<\Theta_2$ in the examination zone 13 irradiated by the fan beam 41.

From the above two equations the following equation is obtained for small angles Θ

$$q \approx a/(2d\lambda) \tag{3}$$

Figure 8:
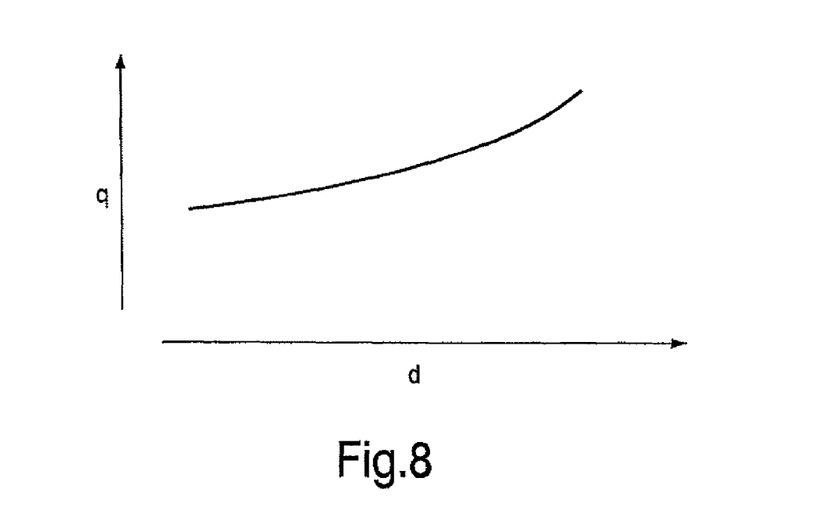
FIG. 8 illustrates the dependence of the amount of the wave vector transfer on the distance between a scatter center in the examination zone and the foot of the detector (point of incidence of the primary beam on the detector unit).

The variation of the value of the wave vector transfer $\vec{q}$ in dependence on the distance d between a scatter center and the foot of the detector thus has the shape of a hyperbola and hence is not linear (shown in FIG. 8). It follows therefrom that the originally linear path of the scattered rays in the (x,y,q) space is curved. The back projection thus takes place along rays curved in the form of a hyperbola.

In the step 111 a voxel V(x,y,q) is determined within a selectable (x,y) zone (field of view or FOV) and within a range of values of the wave vector transfer $\vec{q}$ resulting from the geometry of the computer tomograph.

In the step 113 the filtered values are multiplied by a weighting factor which corresponds to the reciprocal value of the cosine of the scatter angle. The decreasing effective detector surface as a function of an increasing scatter angle is thus taken into account. When said angle is small, the cosine of the angle is practically always 1, so that this weighting can be dispensed with. Moreover, the fact that the radiation density decreases as the distance between the scatter center increases, that is, the voxel V(x,y,q), and the point of incidence of the scattered ray on the measuring surface increases is taken into account by multiplying all measuring values for each radiation source position by a weighting factor which corresponds to the square of the distance between the scatter center, at which the ray associated with the measuring value was scattered, and the point of incidence of the scattered ray on the measuring surface.

When the rebinning is omitted in other versions, an additional multiplication of the filtered measuring values by a weighting factor is necessary; this factor is equal to the reciprocal value of the square of the distance between the radiation source position and the scatter center at which the detected ray was scattered.

During the back projection in the step 115 all curved rays are then taken into account which pass through the voxel V(x,y,q). If not one ray from a radiation source position passes exactly through the center of the voxel, the associated value must be determined by interpolation of the measuring values of neighboring rays. The measuring value that can be associated with the ray passing through the voxel, or the measuring value obtained by interpolation, is accumulated on the voxel V(x,y,q). After the contributions to the relevant voxel have thus been accumulated for all radiation source positions, it is checked in the step 117 whether all voxels in the (x,y,q) zone to be reconstructed have been dealt with. If this is not the case, the flow chart branches to the step 111. Otherwise the scatter intensity distribution has been determined for all voxels in the FOV and the reconstruction method is terminated (step 119).

In other versions the back projection in the volume defined by two linearly independent vectors of the rotational plane and the wave vector transfer can be carried out as an approximation along straight rays.

The invention claimed is:

1. A computed tomography method comprising the steps of:
   a) generating, using a radiation source and a diaphragm arrangement which is arranged between an examination zone and the radiation source, a fan beam which traverses the examination zone and an object present therein,
   b) generating relative motions, comprising a rotation of the radiation source about an axis of rotation and the object,
   c) acquiring measuring values which are dependent on the intensity of the radiation by means of a detector unit which detects, during the relative motions, the primary radiation from the fan beam and radiation which is coherently scattered in the examination zone or on the object, and
   d) reconstructing a CT image of the examination zone from the measuring values, the reconstructing including:
      multiplying the measuring values by a first weighting factor, which corresponds to a square of a distance between a scatter center, at which the detected ray is scattered, and a point of incidence of the scattered ray on the detector unit;
      multiplying the weighted measuring values by a second weighting factor, which corresponds to a reciprocal value of a cosine of the scatter angle; and
      backprojecting, after the steps of multiplying the measuring values by the first and second weighting factors, in a volume which is defined by two linearly independent vectors of a rotational plane and a wave vector transfer.

2. The computed tomography method as claimed in claim 1, in which the back projection during the reconstructing step d) is performed along rays having a curved shape.

3. The computed tomography method as claimed in claim 1, in which prior to the back projection in the reconstructing step d) all measuring values for each radiation source position are multiplied by a weighting factor which corresponds to the reciprocal value of the square of the distance between the radiation source position and the scatter center at which the detected ray was scattered.

4. The computed tomography method as claimed in claim 1, in which the reconstructing step d) comprises the following steps:
   one-dimensional filtering of the measuring values in the direction parallel to the rotational plane,
   rebinning of the measuring values so as to form a number of groups, each measuring value measured by a detector element being associated with an imaginary line from the detector element to a radiation source position and each group comprising a plurality of planes which are parallel to one another and to the axis of rotation and in which a respective line fan is situated,
   reconstruction of the distribution of the scatter intensity from the measuring values, a back projection then being carried out in a volume which is defined by two linearly independent vectors of the rotational plane and a wave vector transfer.

5. The computed tomography method of claim 1, wherein the wave vector transfer is a function of a first distance between a detector element and a foot of the detector unit, a second distance between a scatter center and the foot of the detector unit, and an inverse wavelength of the coherently scattered radiation.

6. The computed tomography method of claim 5, wherein the wave vector transfer is computed based on a function that does not include a scatter angle.

7. The computed tomography method of claim 1, wherein the wave vector transfer is a function of $A/(2D\lambda)$, wherein A represents a distance between a detector element and a foot of the detector unit, D represents a distance between a scatter center and the foot of the detector unit, and $\lambda$ represents the wavelength of the coherently scattered radiation.

8. A computer tomography, comprising
   a radiation source;
   a diaphragm arrangement which is arranged between an examination zone and the radiation source, in order to generate a fan beam which traverses the examination zone,
   a detector unit which is coupled to the radiation source and comprises a measuring surface,
   a drive arrangement for displacing an object present in the examination zone with respect to the radiation source along an axis of rotation and/or parallel to the axis of rotation,
   a reconstruction unit for reconstructing the distribution of the scatter intensity within the examination zone from measuring values acquired by the detector unit, and
   a control unit for controlling the radiation source, the detector unit, the drive arrangement and the reconstruction unit in conformity with the steps a) to d) of claim 1.

9. A computer readable medium containing instructions for controlling a control unit for controlling a radiation source, a diaphragm arrangement, a detector unit, a drive arrangement and a reconstruction unit of a computer tomograph so as to carry out a method comprising:
   a) generating, using the radiation source and the diaphragm arrangement which is arranged between an examination zone and the radiation source, a fan beam which traverses the examination zone,
   b) rotating the radiation source about the examination zone,
   c) acquiring measuring values which are dependent on the intensity of the radiation by means of the detector unit which detects, during the rotation of the source, the primary radiation from the fan beam and radiation which is coherently scattered in the examination zone or on the object, and d) reconstructing a CT image of the examination zone from the measuring values, during which reconstruction a back projection is carried out in a volume which is defined by two linearly independent vectors of the rotational plane and a wave vector transfer, wherein prior to the back projection the measuring values are multiplied by a first weighting factor that corresponds to a square of a distance between a scatter center, at which the detected ray is scattered, and a point of incidence of the scattered ray on the detector unit, and by a second weighting factor that corresponds to a reciprocal value of a cosine of a scatter angle.

10. A computed tomography method, comprising:

generating, using a radiation source and a diaphragm arrangement arranged between an examination zone and the radiation source, a fan beam which traverses the examination zone;

generating a relative motion, comprising a rotation about an axis of rotation, of the radiation source about the examination zone and an object disposed therein;

acquiring measuring values which are dependent on the intensity of the radiation by means of a detector unit which detects, during the relative motion, the primary radiation from the fan beam and radiation which is coherently scattered in the examination zone; and reconstructing a CT image of the examination zone from the measuring values, during which the measuring values are multiplied by a first weighting factor, which corresponds to a square of a distance between a scatter center at which the detected ray is scattered, and a point of incidence of the scattered ray on the detector unit, and by a second weighting factor, which corresponds to a reciprocal value of a cosine of a scatter angle and then a back projection is carried out in a volume which is defined by two linearly independent vectors of a rotational plane and a wave vector transfer, wherein the back projection is performed in the volume along rays having a curved shape.

11. The computed tomography method of claim 10, wherein the curved shape is a hyperbola.

12. The computed tomography method of claim 11, wherein the hyperbola is a function of a distance between a scatter center and a foot of the detector unit.

13. A computed tomography system, comprising:

a detector that detects primary and scattered radiation traversing an examination zone; and a reconstructor that reconstructs measuring values indicative of the detected radiation, wherein the reconstructor back projects the measuring values in a volume as a function of a wave vector transfer that varies based on a difference between a scatter center and a foot of the detector, wherein prior to the back projection the measuring values are multiplied by a first weighting factor, which corresponds to a square of a distance between a scatter center, at which the detected ray is scattered and a point of incidence of the scattered ray on the detector unit, and by a second weighting factor which corresponds to a reciprocal value of a cosine of a scatter angle.

14. The computed tomography system of claim 13, wherein the wave vector transfer is a function of $(1/\lambda)\sin(\theta/2)$, wherein $\lambda$ is the wavelength of the scattered radiation, and $\theta$ is a scatter angle.

15. The computed tomography system of claim 14, wherein the scatter angle is a function of arctan(A/D), wherein A is a distance between a detector element of the detector and a foot of the detector and D is a distance between a scatter center and the foot of the detector.

16. The computed tomography system of claim 13, wherein an intensity of the scattered radiation is dependent exclusively on a scatter material.

* * * * *